United States Patent [19]

Platsoucas

[11] Patent Number: 4,843,004
[45] Date of Patent: Jun. 27, 1989

[54] METHOD FOR THE PRODUCTION OF HUMAN T-T CELL HYBRIDS AND PRODUCTION SUPPRESSOR FACTOR BY HUMAN T-T CELL HYBRIDS

[75] Inventor: Chris Platsoucas, New York, N.Y.

[73] Assignee: Sloan-Kettering Institute for Cancer Research, New York, N.Y.

[21] Appl. No.: 615,889

[22] Filed: May 31, 1984

Related U.S. Application Data

[63] Continuation-in-part of Ser. No. 609,273, May 11, 1984, abandoned.

[51] Int. Cl.$^4$ .................. C12N 5/00; C12P 21/00; C12R 1/91; C07K 15/06
[52] U.S. Cl. .................. 435/240.26; 435/68; 435/172.2; 435/948; 530/351; 530/837; 935/93; 935/101
[58] Field of Search .................. 435/7, 68, 172.2, 240, 435/241, 948, 240.26; 436/548; 424/85; 260/112 R; 530/351, 837; 935/93, 101

[56] References Cited

U.S. PATENT DOCUMENTS

| | | | |
|---|---|---|---|
| 4,434,230 | 2/1984 | Ritts | 435/240 |
| 4,510,244 | 4/1985 | Parks et al. | 435/172.2 |
| 4,544,632 | 10/1985 | Yamamura et al. | 435/172.2 |
| 4,665,032 | 5/1987 | Laurence | 435/68 |
| 4,728,614 | 3/1988 | Lau | 435/68 |

FOREIGN PATENT DOCUMENTS 2108528  5/1983  United Kingdom .................. 435/68

OTHER PUBLICATIONS

Arnold, Bernd; "Selection of T-Cell Hybridomas by the Fluorescence-Activated Cell Sorter"; *Monoclonal Antibodies and T-Cell Hybridomas*, ed. Hämmerling et al., ©1981; pp. 560 and 561.

Davis et al., "A Simple Single-Step Technique for Selecting and Cloning Hybridomas for the Production of Monoclonal Antibodies"; *J. Immunol. Methods*, vol. 50 (1982); pp. 161-171.

Gershon et al.; "Properties of a Somatic Hybrid between Mouse Cells with Different Genotypes"; *Nature*, vol. 198 (1963); pp. 912-913.

Laurence, J. et al.; "Soluble Suppressor Factors in Patients with Acquired Immune Deficiency Syndrome and Its Prodrome"; *J. Clin. Invest.*, vol. 72, Dec. 1983, pp. 2072-2081.

Greene et al., "Production of Human Suppressor T Cell Hybridomas", J. of Immunology, vol. 129, No. 5, pp. 1986-1992 (1982).

Grillot-Courvalin et al., "Establishment of a Human T-Cell Hybrid Line with Suppressive Activity", Nature, vol. 292, pp. 844-845 (1981).

*Primary Examiner*—Elizabeth C. Weimar
*Attorney, Agent, or Firm*—John P. White

[57] ABSTRACT

A new method is described for fusing and selecting human-human hybrid cells. The selection process begins after longer incubation times in culture medium and involves selection without using HAT or any other drug regimen. Certain T-T cell hybrids produced in this manner secrete suppressor factor.

3 Claims, No Drawings

METHOD FOR THE PRODUCTION OF HUMAN T-T CELL HYBRIDS AND PRODUCTION SUPPRESSOR FACTOR BY HUMAN T-T CELL HYBRIDS

This invention was made in part with government support under CA 32070 awarded by the National Cancer Institute. The government has certain rights in this invention.

This application is a continuation-in-part of previously filed U.S. application Ser. No. 609,273, filed May 11, 1984, now abandoned.

This invention relates to a method of making human hematopoietic hybrid cells such as human hematopoietic hybrid cells and especially T-T cell hybrids. Some of these T-T cell hybrids produce suppressor factor (SF) which suppresses cellular proliferation and antibody production and would be useful to control disorders such as those involving abnormal cellular proliferation. Some of the human T-T cell hybrids produce B-cell growth factor (BCGF).

SUMMARY

A method has been developed for the production of human hematopoietic cell hybrids especially T-T cell hybrids as determined by HLA typing.

Some of these T-T cell hybrids produce factors useful for biotherapy or exhibiting specific-immunological functions. This is accomplished by fusing cells from human T cell lines with appropriately sensitized or induced human T cells exhibiting specific immunological function or producing the desired factors. According to the procedure of the invention, selection in HAT medium, that may be toxic to certain hybridomas is not required. (HAT=hypoxanthine-aminopterin-thymidine).

The method is shown to fuse lymphocytes of T cell line cells but it makes possible the production of B cell hybridomas which may then produce human or other monoclonal antibodies.

DESCRIPTION

The following references have dealt with T-T cell hybrids:
Irigoyen, O. et al. (1981) J. Exp. Med. 154:1827.
Okada, M. et al. (1981) Proc. Natl. Acad. Sci. U.S.A. 78:7717.
Butler, J. L., et al. (1983) J. Exp. Med. 157:60.
Kobayashi et al., (1982) J. Immunol. 128:2714.
Asada et al., (1983) Cellular Immunology, 77:150.
Le, J. et al, (1982) Proc. Natl. Acad. Sci. U.S.A. 79:7857.
Foung et al., (1982) Proc. Natl. Acad. Sci. U.S.A. 79:7484.
DeFreitas, E. C., et al, (1982) Proc. Natl. Acad. Sci. U.S.A. 79:6646.
Trucco, M., (1984) Nature 309:166.

Also there is some previous description of T-T cell hybrids which produce SF:
Grillot - Courvalin, Catherine et al. (1981) Nature 292:844.
Greene, Warner, C., et al. (1982) J. Immunol. 129:1986.
Taussig, M. J., et al. (1979) Nature 277: at 305 and 308.
Kontianen, Sirkka et al. (1978) Nature 274:477.

The method of the invention differs from all of the above in that:
1. HAT medium is not used
2. HGPRT negative or any other drug sensitive mutants of the lymphoplastoid T cell line are not needed.
3. Selection of the hybrids has been accomplished by cloning in agar and limiting dilution methods and has been done on the basis of their functional properties and the expression of HLA antigens. Factor(s) have been identified which suppress not only mitogen or antigen (alloantigen) driven cellular proliferation of human peripheral blood leukocytes but also antibody production (U.S. Pat. application Ser. No. 609,273 filed May 11, 1984, now abandoned).

Such factor(s) have potential use for example in the treatment of patients with cancer, graft versus host disease(s), autoimmune disease(s) and lympho-proliferative malignancy disorder(s) such as leukemia.

Previous suppressor factors have been reported in the literature [See Grillot-Courvalin, Catherine et al., (1981) Nature 292:844; Greene, Warner C., et al. (1982) J. Immunol. 129:1986; M. J. Taussig, et al. (1979) Nature 277: at 305 and 308; Sirkka Kontianen, et al. (1978) Nature 274:477; Eisenthal, A., et al. (1979) Ann N.Y. Acad. Sci. 332:367; Smith, R. T., et al. (1970) Am. J. Pathol. 60:495; Namba, Y., et al. (1975) Inflammation 1:5; Lee, S.C., et al. (1977) J. Immunol. 118:88; Jeogosothy, B. V., et al. (1979) J. Exp. Med. 150:622; Namba, Y., et al. (1977) J. Immunol. 118:1379; Jegosathy, B. V., et al. (1976) 193:1260; and Waksman, B. H., et al. (1978) Cell Immunol. 36:180].

The suppressor factor(s) described are different from all these factors above because they: (1) exhibit different functional properties, (2) exhibit different molecular weight; (3) are produced constitutively and in substantially higher quantities.

Stable human hybridomas such as T-T cell hybrids were developed by fusing cells from human lymphoblastoid cell lines such as T cell lines (e.g., Jurkat or Molt-4) with human lymphocytes such as peripheral blood T cells stimulated with mitogens such phytohaemagluttinin (PHA), Concanavalin A (Con A), Staphylococcus Enterotoxin A (SEA) or with allogeneic cells in mixed lymphocyte MLC).

The hybrids were selected by cloning in agar and by limiting dilution methods described below.

Stimulation of peripheral blood lymphocytes with mitogens or allogeneic cells in MLC Human peripheral blood mononuclear leukocytes (MNC) from normal donors were adjusted at a concentration $2 \times 10^6$ cells/ml and were cultured with optimal concentrations of Con A or PHA or SEA (PHA 5–10 micrograms/ml, Con A 2–25 micrograms/ml and 0.01–0.1 micrograms/ml of SEA).

The cells were cultured for 2–4 days, then washed three times with RPMI 1640 supplemented with 10% heat inactivated fetal calf serum (FCS) and fused with lymphoblastoid T cell lines as described.

Alternatively, E-Rosette forming cells were isolated from mitogen-stimulated MLC by rosetting with sheep erythrocytes by the method described below.

In other experiments human peripheral blood mononuclear leukocytes at a concentration of approximately $2 \times 10^6$ cells/ml were stimulated with allogeneic mononuclear cells as for example $2 \times 10^6$ cells/ml irradiated at 2500 rads. Cells were washed $3\times$ with RPMI 1640 supplemented with 10% heat inactivated FCS and fused with lymphoblastoid T cell lines as described.

Human lymphoblastoid T cell line

Cells of the Jurkat T cell line were grown in RPMI 1640 medium supplemented with 10% heat-inactivated fetal calf serum, 25 mM Hepes buffer, 2 mM L-glutamine, 100 U/ml penicillin and 100 micrograms/ml of streptomycin.

Fusion for Hybrid Cell Production

Human peripheral blood mononuclear leukocytes or purified T cells stimulated with mitogens or allogeneic cells in MLC were washed 3× with serum-free RPMI 1640. Cells from the Jurkat lymphoblastoid T cell line or other cell lines employed were so washed.

Mitogen or alloantigen activated mononuclear cells or T-lymphocytes were mixed in a single tube with cells from a T cell line such as a lymphoblastoid T cell line as Jurkat at appropriate ratios such as 10/1. The cells were centrifuged for 10 min at 400×g. The supernatant was removed and discarded and the mixed cell pellet was disrupted and dispersed by gentle agitation.

1 ml of pre-warmed (37° C.) fusion medium (50% polyethylene glycol in RPMI 1640) was added dropwise to the cell pellet and the mixture was agitated by rocking the tube gently by hand for one minute (moving the tube through an arc of a circle of about 90° is found to work well). 1 ml of pre-warmed (37° C.) serum-free RPMI 1640 was added slowly and the tube was rolled gently between the hands for about one minute.

Two ml of pre-warmed serum-free RPMI 1640 was added and the tube was rolled gently between the hands for about two minutes.

Four ml of prewarmed RPMI 1640 supplemented with 10% heat-inactivated FCS were added and the tube was rolled between the hands for about three minutes.

Eight ml of prewarmed RPMI 1640 supplemented with 10% heat-inactivated FCS and the tube was gently rolled between the hands for another three minutes.

The cells were centrifuged for ten minutes at 400 g, and re-suspended very gently in RPMI 1640 supplemented with 15–20% heat-inactivated fetal calf-serum, 25 mM Hepes, 2 mM L-glutamine, 100 U/ml penicillin, 100 micrograms/ml streptomycin.

The cells were incubated at 37° C. in a humidified incubator with 5% $CO_2$.

Hybridoma selection procedure

After incubation for appropriate time intervals (1–60 days) at 37° C. the cells were twice washed with RPMI 1640 supplemented with 10% heat-inactivated fetal calf serum (FCS), and appropriate number of cells in this medium were mixed with appropriate volumes of semisolid medium such as 1% agar in RPMI 1640 supplemented with 15% heat-inactivation FCS, 2 mM L-glutamine, 25 mM Hepes 100 U/ml penicillin, 100 micrograms/ml streptomycin to achieve a final concentration of about 0.3% agar. The cells and the agar were mixed immediately and the cells were transferred quickly to appropriate-sized petri dishes such as 100 mmm. Other semi-solid media may be used as well as agar. (It had been standard procedure in the art of hybridoma selection to incubate cells for two days and then transfer them to HAT medium. In this invention such a medium or any other toxic medium is not used). In this invention the best times for transfer to semi-solid medium after incubation were found to be 10, 15 and 20 days. Other sufficient incubation times might be 5 days or 3 days etc. for example.

The agar was allowed to solidify at room temperature and the petri dishes were transferred to a humidified 37° C. incubator with 5% $CO_2$. Growth of colonies was revealed by macro- or microscopic inspection at 7–40 days.

Individual colonies were transferred to 96-well flat-bottomed well plates and 100 microliters of RPMI 1640 supplemented with 20% heat-inactivated FCS, 25 mM Hepes, 2 mM L-glutamine, 100 U/ml penicillin, 100 microgram/ml streptomycin was added per well.

In certain experiments these wells contained feeder cultures consisting of irradiated (with 2500 rads) human peripheral blood mononuclear leukocytes, whose lymphocytes were used as a fusion partner or possibly from other donors.

Supernatants or hybrids from wells exhibiting cell growth were expanded and screened for functional prpperties using the methods described below.

Hybrids with functional properties were HLA typed and cytogenetically analyzed. Alternatively, one could screen first by HLA or T cell differentiation antigen expression and then determine functional properties of hybrids so selected. Cells producing factors useful for biotherapy or exhibiting specific biological functions of interest were further re-cloned several times by limiting dilution methods at the level of 0.2–0.4 cells/well in RPMI 1640 containing 15–20% heat-inactivated FCS, 25 mM Hepes, 2 mM L-glutamine, 100 U/ml penicillin, 100 micrograms/ml streptomycin.

Feeder layers were employed comprising approximately 25,000–100,000 irradiated human peripheral blood mononuclear leukocytes preferably from the same donor used as a fusion partner or from a different donor.

The cell surface phenotype of these hybrids is T3+ T4+ T8−. However, using these methods hybrids of other phenotypes can be developed. The examples above serve to illustrate the invention and not to limit the invention to the examples shown.

ISOLATION OF PERIPHERAL BLOOD MONONUCLEAR LEUKOCYTES

Depletion of Monocytes

Mononuclear cells from normal donors were isolated by centrifugation on a Ficoll/Hypaque density cushion (Boyum, A. (1968) Scand. J. Clin. lab. Invest. 21:(Suppl. 97) 77), at room temperature. The cells were washed three times in Hanks' balanced salt solution (HBSS) and resuspended in RPMI-1640 containing 15% heat-inactivated fetal calf serum at a concentration of $4 \times 10^6$ cells/ml. Lymphocyte separator reagent (Technicon Instrument Co., Tarrytown, N.Y.) was added to the mononuclear cell suspension at a volume ratio of 1:2 and the mixture was incubated at 37° C. on a rotator for 30 min. Phagocytic cells were depleted by subsequent centrifugation at 400×g for 20 min on a Ficoll/Hypaque density cushion. Lymphoid cells depleted of phagocytic cells were collected from the interface, washed three time with Hank's balanced salt solution (HBSS) and resuspended at $4 \times 10^6$ cells/ml.

Preparation of T lymphocytes

T lymphocytes were prepared by rosetting with neuraminidase-treated sheep erythrocytes (SRBC) (25 units/ml. of 5% SRBC) followed by centrifugation on ficoll/Hypaque as previously described [Platsoucas et al. (1980) J. Immunol. 125:1216]. Two-milliliter aliquots of lymphocytes ($4\times10^6$/ml) in HBSS were mixed with 0.5 ml of heat-inactivated and SRBC-absorbed fetal calf serum and 2 ml of 1% neuraminidase treated SRBC. The mixture was incubated for 5 min at 37° C., centrifuged for 5 min at $200\times G$, and incubated at 4° C. for an additional hour. The rosettes were resuspended carefully and incubated on ice for an additional 15 min. The cell suspensions were layered on a Ficoll/Hypaque density cushion and centrifuged at $400\times G$ for 20 min at controlled temperature (22° C.). Non-T cells were recovered from the interface and were washed three times with HBSS. Rosetting T cells were recovered from the pellets after lysis of attached SRBC by Tris-buffered 0.83% ammonium chloride (pH 7.2). The T cells were washed three times with HBSS. E-rosetting cells prepared by this method were more than 95% T lymphocytes, as determined by rerosetting with SRBC without nonspecific esterase-positive cells and less than 2% immunoglobulin-bearing cells. E-rosette-negative cells contained more than 70% surface immunoglobulin cells, as determined by immunofluorescence, and less than 1% of E-rosette forming cells or non-specific esterase positive cells. These cells were used as B cells. B cells are used for B cell growth factor assay.

Proliferative Response to Mitogens

Human peripheral blood mononuclear leukocytes (at a concentration of $1\times10^6$ cells/ml) were cultured in RPMI-1640 containing 10% fetal calf serum and supplemented with 25 mM Hepes, 2 mM L-glutamine and 100 units/ml Penicillin and 100 micrograms/ml streptomycin. One hundred microliters of the cell suspension were stimulated on U-microliter plates (Scientific Products) by various concentration of mitogens (PHA-P, Con A, PWM) at 37° C. in a humidified incubator in a 5% $CO_2$, 95% air environment. The cultures were pulsed with 25 microliters of tritiated thymidine (specific activity, 6.7 Ci/mmol, New England Nuclear, Boston, Mass.) after 72 hours and harvested using an automatic cell harvester 24 hours after the addition of the isotopes.

Mixed Lymphocyte Culture

Human peripheral blood mononuclear leukocytes from various donors were prepared as above.

Responding cells ($1\times10^5$) were cultured with $1\times10^5$ stimulating cells in round bottom microtiter plates in total volume of 0.2 ml. The stimulating cells were inactivated by x-irradiation (2000 rads). The culture medium is RPMI-1640 supplemented with 10% heat-inactivated fetal calf-serum, 25 mM Hepes, 2 mM L-glutamine, penicillin (100 units/ml) and streptomycin (100 microgram/ml). The cultures were incubated at 37° C. in a humidified atmosphere with 5% $CO_2$, pulsed the 5th day with 1 micro Ci/well of $^3$H-thymidine (New England Nuclear, Boston, Mass., specific activity 6.7 Ci/mmole) and harvested 24 hours later on an automatic cell harvester (Skarton, Norway). All cultures were performed in quadruplicate.

Natural Killer Cytotoxicity

Natural killer cytotoxicity was determined as previously described (Platsoucas, et al. (1980) J. Immunol. 125:1216). Target cells of the K562 and Molt-4 lines, maintained in RPMI-1640 supplemented with 10% fetal calf serum, glutamine and antibiotics as above were labelled with 300 microliters of $^{51}$Cr per $2\times10^6$ cells [sodium ($^{51}$Cr) chromate, New England Nuclear, Boston, Mass.] for 2 hours. The target cells were washed three times and then resuspended in the same medium, at a concentration of $5\times10^4$ cells/ml. Effector lymphocytes were washed three times in RPMI-1640 supplemented with 10% fetal calf serum, arranged at the appropriate concentration and one hundred microliters were added to one hundred microliters of target cells in U-bottom microtiter plates (Nunclon, Denmark), to achieve effector to target ratios 100:1, 50:1, and 25:1 etc. The plates were centrifuged at $40\times g$ for 2 min and subsequently incubated at 37° C. in a humidified 5% $CO_2$ atmosphere. After 4 hours, the plates were centrifuged at $500\times g$ for 5 min and 100 microliters of the supernatants were collected and counted for $^{51}$Cr release in a well-type Auto-Gamma scintillation counter.

Percent specific lysis is calculated by the formula:

$$\% \text{ Specific lysis} = \frac{E-S}{T-S} \times 100$$

where E=mean cpm released in the presence of effector cells. S=mean cpm spontaneously released by target cells incubated with medium alone, and T=mean cpm released after treating target cells with Triton$\times$100 (1:100 dilution).

Cell Viability

Peripheral blood mononuclear leukocytes (MNL) were cultured at a concentration of $1\times10^6$ cells/ml in RPMI 1640 supplemented with 10% heat-inactivated FCS, 25 mM herpes buffer, 2 mM L-glutamine, and the antibiotics streptomycin 100 micrograms/ml and penicillin 100 U/ml for up to 88 hrs.

Control samples were incubated in the above medium and test samples are incubated with SF produced by Jurkat et al cell lines. Samples were withdrawn at 20 hrs, 44 hr, 68 hrs and 88 hrs. Cells twice were washed and viability was determined by Trypan blue dye exclusion.

M.W. determinations

These were carried out by AcA-44 ultrogel (LKB) filtration in isotonic prosphate buffered saline (PBS). Molecular weight markers employed involved:
Bovine serum albumin: 68,000 M.W.
Ovalbumin: 43,000 M.W.
Cytochrome c: 11,700 M.W.

Induction of de novo Ig synthesis and secretion by human peripheral blood mononuclear leukocytes in the PWM - induced differentiation system Human peripheral blood mononuclear leukocytes were cultured at $1\times10^6$ cells/ml in RPMI-1640 supplemented with 10% heat inactivated fetal calf serum, 2 mM glutamine, Hepes and antibiotics as previously described, in total volume of 2 ml, for 7 days at 37° C. in 5% $CO_2$ in a humidified incubator. Pokeweed mitogen (10 microgram/ml, optimal concentration; Grand Island Biological Co., Grand Island, N.Y.) was added from the beginning of the culture. After incubation for 7 days the tubes were centrifuged at $400\times g$ and supernatants were carefully withdrawn and stored at $-20°$ C. until assayed for immunoglobulin.

Determination of De Novo IgG, IgA, IgM Immunoglobulins by Enzyme-linked Immunoabsorbent Assay (ELISA)

These determinations were carried out by a modification of the method described by Engvall and Perlmann J. Immunol. 109:129 (1972). Rabbit anti-human immunoglobulin antibody, heavy chain specific (mu, gamma or alpha) (Accurate Chemical) were arranged at a concentration of 5 g/ml in 0.10 M Na , pH 9.6, containing 0.05% sodium azide. Two hundred microliters of antibody solution per well were transferred into 96-well round bottom microliter plates and incubated at 37° C. for 3 hours. The plates were stored at 4° C. until use and were stable for over two weeks. Before use the plates and were washed with PBS containing 0.02% Tween 20 three times, were allowed to remain at room temperature for 5 min, between washings. Several dilutions of the unknown immunoglobulin containing supernatants were prepared in PBS containing 0.02% Tween 20 and volumes of 0.2 ml will be transferred to the plates. The plates were incubated for 5 hours at room temperature, on a rocket platform.

Supernatants were removed by aspiration and the tubes were washed three times with PBS, containing 0.02% Tween 20. Alkaline phosphatase conjugated rabbit anti-human immunoglobulin antibody heavy chain specific was obtained from AMF Immunoreagents Inc., Sequin, Tex. (gamma, mu, or alpha heavy chain specific). Before use the conjugates were absorbed with 1% ovalbumin solution in phosphate buffered saline (1 hour at room temperature), to absorb extra glutaraldehyde. One ml of conjugate diluted 1:500 with PBS- Tween 20, was added to the anti-human Ig-human Ig coated tubes, and the tubes were incubated for 16 hours at room temperature. Subsequently, the unbound conjugate was removed by washing the plates three times with PBS- Tween 20. The amount of bound alkaline phosphatase rabbit anti-human heavy chain specific, was determined using p-nitrophenylphosphate (NPP) (Sigma) as a substrate. One ml of 1 mg/1 NPP, in 0.05 M sodium carbonate buffer (pH 9.8) containing $10^{-3}$M MgCl was added to the plates and the released p-nitrophenolate was measured at 405 nm after one hour, using a titertek ELISA reader. Standard curves were constructed using purified IgG, IgA or IgM immunoglobulins for polyclonal immunoglobulin secretion, or purified paraproteins from patients with multiple myeloma for the determination of idiotypic immunoglobulin secretion.

PBS = phosphate buffered saline

Interferon Determination

Alpha and gamma interferons were determined by the standard cytopathic effect reduction assay using vesicular stomatitis virus challanged human fibroblasts trisomic for chromosome 21, or bovine kidney cells (MDBK cells).

Titers of interferons were determined by the reciprocal of the highest dilution which inhibited the cytopathic effect by 50%. In other experiments, monoclonal or polyclonal antibodies specific for alpha or gamma interferons were added to the mononuclear cells immediately before the addition of PHA and the SF(s). These monoclonal antibodies did not block the inhibition by the SF(s) of the proliferative responses of MIC to PHA.

Lymphotoxin or TNF was determined by the in vitro method of Carswell, E. et al. (1975) Proc. Nat'l. Acad. Sci. USA 72:3666.

BCGF Assay

The method of Muraguchi, A. and A. S. Fauci (1982) J. Immunol. 129:1104 was used.

Factor(s) were described and identified which inhibit leukocyte proliferative responses. In particular these factor(s), suppressor factor (SF), have been found to be produced by hematopoietic cells such as human lymphoblastoid cell lines—especially T cell lines and others such as B cell lines or erythroleukemic cell lines. Particular T cell lines known to produce supressor factor(s) are Jurkat, HPB-ALL, TALL-1, HD-MAR, SKW-3, DND 41, HPB-MLT and MOLT-4. Erytholeukemic cell lines such as K-562 can also produce SF. B cell lines such as CESS can also produce SF. This data is seen in U.S. Pat. application Ser. No. 609,273 filed May 11, 1984 now abandoned.

Supernatants from such cells inhibit the proliferative responses of T-lymphocytes to mitogens such as phytohemagglutinin (PHA), concanavalin A (CON A) and poke-weed mitogen (PWM). (Tables I–III)

It also inhibits the proliferative responses of T-cells to allogeneic cells in mixed lymphocyte culture (MLC). (Table IV)

Also this factor(s) inhibits antibody production of blood cells, and especially in vitro by human peripheral blood mononuclear leukocytes in the PWM-driven system (Table V). SF may inhibit certain proliferative responses of B-cells.

The action of SF appears to be cytostatic not cytotoxic since it:

(1) does not affect the viability of human peripheral blood mononuclear leukocytes in culture after a four day incubation (Table VI);

TABLE IA

Inhibition of proliferative response of peripheral blood mononuclear leukocytes to PHA, by SF produced by the Jurkat, HPB-All and Molt 4 lines

| | PROLIFERATIVE RESPONSES (CPM) | | | | | |
|---|---|---|---|---|---|---|
| | Jurkat | | HPB-All | | Molt-4 | |
| % SF (v/v) | CPM | % suppression | CPM | % suppression | CPM | % suppression |
| medium | 513 ± 175 | — | 513 ± 175 | — | 513 ± 175 | — |
| medium + PHA | 11058 ± 1883 | — | 11058 ± 1883 | — | 11058 ± 1883 | — |
| medium + PHA + 0.015% SF | 2351 ± 223 | 79% | 6318 ± 1689 | 43% | 2399 ± 339 | 78% |
| medium + PHA + 0.05% SF | 2612 ± 337 | 76% | 2199 ± 1792 | 35% | 1118 ± 28 | 89% |
| medium + PHA + 0.1% SF | 2861 ± 269 | 74% | 8800 ± 2172 | 20% | 998 ± 105 | 91% |
| medium + PHA + | 4404 ± 390 | 60% | 1778 ± 111 | 84% | 1333 ± 328 | 88% |

TABLE IA-continued

Inhibition of proliferative response of peripheral blood mononuclear leukocytes to PHA, by SF produced by the Jurkat, HPB-All and Molt 4 lines

| | PROLIFERATIVE RESPONSES (CPM) | | | | | |
|---|---|---|---|---|---|---|
| | Jurkat | | HPB-All | | Molt-4 | |
| % SF (v/v) | CPM | % suppression | CPM | % suppression | CPM | % suppression |
| 0.5% SF medium + PHA + | 3921 ± 277 | 65% | 1419 ± 234 | 87% | 1127 ± 77 | 89% |
| 0.95% SF medium + PHA + | 4156 ± 256 | 62% | 1564 ± 156 | 86% | 1130 ± 138 | 89% |
| 1.9% SF medium + PHA + | 4426 ± 354 | 60% | 2186 ± 265 | 80% | 1240 ± 82 | 89% |
| 3.75% SF medium + PHA + | 3512 ± 302 | 68% | 2335 ± 319 | 79% | 985 ± 36 | 91% |
| 15% SF medium + PHA + | 3538 ± 571 | 68% | 2685 ± 236 | 76% | 728 ± 57 | 93% |
| 30% SF | | | | | | |

TABLE IB

Inhibition of proliferative response of peripheral blood mononuclear leukocytes to PHA, by SF produced by the K562, HPB-All, Molt-4 and CESS tumor cell lines

| | PROLIFERATIVE RESPONSE (CPM) | | | | | | | |
|---|---|---|---|---|---|---|---|---|
| | K562 | | Molt-4 | | Cess | | HPB-LL | |
| % SF (v/v) | CPM | % suppression | CPM | % suppression | CPM | % suppression | CPM | % suppression |
| medium | 2279 ± 14 | — | 2279 ± 14 | — | 2279 ± 14 | — | 2279 ± 14 | — |
| medium + PHA | 56211 ± 3811 | — | 56211 ± 3811 | — | 56211 ± 3811 | — | 56211 ± 3811 | — |
| medium + PHA + 1.87% SF | 1624 ± 88 | 97% | 1499 ± 248 | 97% | 48729 ± 4699 | 13% | 8124 ± 399 | 86% |
| medium + PHA + 3.75% SF | 1515 ± 190 | 97% | 1287 ± 130 | 98% | 51048 ± 6139 | 9% | 8109 ± 816 | 86% |
| medium + PHA + 7.5% SF | 2091 ± 942 | 96% | 1249 ± 132 | 98% | 53579 ± 3152 | 5% | 6687 ± 773 | 88% |
| medium + PHA + 15% SF | 1536 ± 119 | 97% | 1225 ± 143 | 98% | 59898 ± 5211 | 6% | 7916 ± 1116 | 86% |
| medium + PHA + 30% SF | 2009 ± 254 | 96% | 865 ± 101 | 98% | 31823 ± 1550 | 43% | 5434 ± 777 | 90% |

TABLE 1C

Inhibition of proliferative response of human peripheral blood mononuclear leukocytes to PHA, by SF produced by TALL-1, HD-Mar, SKW-3, DND-41 and HPB-MLT

| | Cell line Supernatant** | CPM | % Suppression |
|---|---|---|---|
| MNC* | None | 4677 ± 1367 | |
| MNC + PHA | None | 93646 ± 9369 | |
| MNC + PHA | TALL-1 | 18119 ± 3822 | 81 |
| MNC + PHA | HD-Mar | 9914 ± 1182 | 89 |
| MNC + PHA | SKW-3 | 9268 ± 434 | 90 |
| MNC + PHA | DND-41 | 28633 ± 3356 | 69 |
| MNC + PHA | HPB-MLT | 12136 ± 342 | 87 |

*MNC: Human, eripheral blood mononuclear leukocytes.
**Cell line supernatants were employed at concentration of 25% (v/v).

TABLE II

Inhibition of proliferative response of peripheral blood mononuclear leukocytes to CON A, by SF produced by the Jurkat, HPB-All and Molt 4 lines

| | PROLIFERATIVE RESPONSES (CPM) | | | | | |
|---|---|---|---|---|---|---|
| | Jurkat | | HPB-All | | Molt-4 | |
| % SF (v/v) | CPM | % suppression | CPM | % suppression | CPM | % suppression |
| medium | 265 ± 47 | — | 265 ± 47 | — | 265 ± 47 | — |
| medium + CON A + | 40792 ± 7959 | — | 40792 ± 7454 | — | 40792 ± 7454 | — |
| medium + CON A + 0.015% SF | 3916 ± 239 | 90% | 61751 ± 13610 | — | 14440 ± 6966 | 65% |
| medium + CON A + 0.05% SF | 3606 ± 379 | 91% | 31713 ± 11104 | 22% | 4814 ± 580 | 88% |
| medium + CON A + 0.1% SF | 3889 ± 413 | 90% | 12399 ± 2129 | 69% | 4126 ± 681 | 90% |
| medium + CON A + 0.5% SF | 4489 ± 649 | 89% | 6414 ± 1356 | 84% | 3233 ± 688 | 92% |
| medium + CON A + 0.95% SF | 3671 ± 294 | 91% | 3886 ± 1055 | 90% | 2718 ± 910 | 93% |

TABLE II-continued

Inhibition of proliferative response of peripheral blood mononuclear leukocytes to CON A, by SF produced by the Jurkat, HPB-All and Molt 4 lines

| | PROLIFERATIVE RESPONSES (CPM) | | | | | |
|---|---|---|---|---|---|---|
| | Jurkat | | HPB-All | | Molt-4 | |
| % SF (v/v) | CPM | % suppression | CPM | % suppression | CPM | % suppression |
| medium + CON A + 1.9% SF | 3615 ± 211 | 91% | 3678 ± 765 | 91% | 2244 ± 446 | 94% |
| medium + CON A + 3.75% SF | 3649 ± 350 | 91% | 3879 ± 734 | 90% | 26622 ± 401 | 93% |
| medium + CON A + 15% SF | 3605 ± 191 | 91% | 3421 ± 404 | 92% | 1729 ± 108 | 96% |
| medium + CON A + 30% SF | 3862 ± 381 | 91% | 3637 ± 296 | 91% | 855 ± 48 | 98% |

TABLE III

Inhibition of proliferative response of peripheral blood mononuclear leukocytes to PWM by SF produced by the Jurkat tumor cell line

| | PROLIFERATIVE RESPONSES (CPM) Jurkat | |
|---|---|---|
| % SF (V/V) | CPM | % suppression |
| Medium | 703 ± 84 | — |
| Medium + PWM | 13119 ± 1792 | — |
| Medium + PWM + 1.56% SF | 4631 ± 389 | 65% |
| Medium + PWM + 3.12% SF | 4560 ± 373 | 65% |
| Medium + PWM + 6.25% SF | 3624 ± 381 | 72% |
| Medium + PWM + 12.5% SF | 4474 ± 306 | 66% |
| Medium + PWM + 25% SF | 5095 ± 352 | 61% |

TABLE IV

Inhibition by SF produced by the Jurkat tumor cell lines, of the proliferative responses of human peripheral blood mononuclear leukocytes to allogeneic cells in mixed lymphocyte culture

| | PROLIFERATIVE RESPONSES (CPM) Jurkat | |
|---|---|---|
| % SF (v/v) | CPM | % suppression |
| Medium | 7382 | — |
| Medium + 1.56% SF | 3849 | 48% |
| Medium + 3.12% SF | 3229 | 56% |
| Medium + 6.25% SF | 3922 | 47% |
| Medium + 12.50% SF | 3678 | 50% |
| Medium + 25.00% SF | 6159 | 17% |

TABLE V

Inhibition of de novo immunoglobulin synthesis and secretion of human peripheral blood mononuclear leukocytes in the PWM-induced differentiation system, by SF produced by the Jurkat, HPB-ALL, Molt-4, K562 and CESS CELL LINES.

| | Cell line Supernatants Dilutions | Immunoglobulin* | | |
|---|---|---|---|---|
| | | IgM (microg/dl) | IgA (microg/dl) | IgG (microg/dl) |
| Mononuclear cells + PWM | None | 243.0 | 70.5 | 54.3 |
| | Jurkat | | | |
| MNC + PWM | 1:3 | 19.0 | l.t. 2.0 | l.t. 2.0 |
| MNC + PWM | 1:50 | 20.5 | l.t. 2.0 | ND |
| MNC + PWM | 1:1000 | 15.0 | 3.75 | ND |
| MNC + PWM | 1:10000 | 19.0 | 4.5 | ND |
| | HPB-ALL | | | |
| MNC + PWM | 1:3 | 10.5 | l.t. 2.0 | l.t. 2.0 |
| MNC + PWM | 1:50 | 35.0 | 5.7 | l.t. 2.0 |
| MNC + PWM | 1:1000 | 27.3 | 11.3 | l.t. 2.0 |
| MNC + PWM | 1:10000 | 22.3 | 13.0 | l.t. 2.0 |
| | Molt-4 | | | |
| MNC + PWM | 1:3 | 23.5 | l.t. 2.0 | ND |
| MNC + PWM | 1:50 | 36.7 | 14.3 | l.t. 2.0 |
| MNC + PWM | 1:1000 | 35.7 | 16.0 | l.t. 2.0 |
| | K562 | | | |
| MNC + PWM | 1:3 | 9.9 | l.t. 2.0 | ND |
| MNC + PWM | 1:50 | 17.8 | l.t. 2.0 | l.t. 2.0 |
| MNC + PWM | 1:1000 | 18.3 | 9.0 | ND |
| | CESS | | | |
| MNC + PWM | 1:3 | 12.2 | l.t. 2.0 | 10.3 |
| MNC + PWM | 1:50 | 18.0 | l.t. 2.0 | ND |
| MNC + PWM | 1:1000 | 18.3 | 11.2 | ND |

*Determined by ELISA
ND—not determined
l.t.—less than

TABLE VI

The viability of peripheral blood mononuclear leukocytes is not affected by prolonged incubation with SF produced by the Jurkat* tumor cell lines

| Tumor cell lines | % Viability Duration of treatment | | | |
|---|---|---|---|---|
| | 20 hrs | 44 hrs | 68 hrs | 88 hrs |
| Medium * alone | 98% | 100% | 96% | 93% |
| Jurkat | 99% | 96% | 95% | 90% |

*This effect is also seen with HPB-ALL, K562 and Molt-4 supernatants.

TABLE VII

Suppressor factor(s) preparations produced by the Jurkat cell lines do not affect natural killer cytotoxicity: mediated by peripheral blood mononuclear leukocytes, against K562 targets

| | % Cytotoxicity Effector to target ratio | | | |
|---|---|---|---|---|
| | Donor 1 | | Donor 2 | |
| SF Source | 50:1 | 25:1 | 50:1 | 25:1 |
| Medium | 66 | 59 | 58 | 50 |
| Jurkat | 68 | 56 | 51 | 40 |

TABLE VIII

Inhibition of the growth of human lung tumor cell lines by SF - containing supernatants form the Jurkat, HPB-ALL, K562 and Molt-4 human tumor cell lines

| | Cell Numbers Lines | | | | | |
|---|---|---|---|---|---|---|
| | SK-LC-6 Hours of Treatment | | | SK-LC-14 Hours of Treatment | | |
| Cell line Supernatants* | 0 | 60 | 90 | 0 | 60 | 90 |
| None | $0.5 \times 10^5$ | $1.4 \times 10^5$ | $5.7 \times 10^5$ | $0.5 \times 10^5$ | $1.7 \times 10^5$ | $4.2 \times 10^5$ |
| Jurkat | $0.5 \times 10^5$ | $0.6 \times 10^5$ | $1.5 \times 10^5$ | $0.5 \times 10^5$ | $1.4 \times 10^5$ | $1.9 \times 10^5$ |
| HPB-All | $0.5 \times 10^5$ | $1.1 \times 10^5$ | $1.4 \times 10^5$ | $0.5 \times 10^5$ | $2.1 \times 10^5$ | $3.0 \times 10^5$ |
| K562 | $0.5 \times 10^5$ | $0.6 \times 10^5$ | $1.2 \times 10^5$ | $0.5 \times 10^5$ | $0.7 \times 10^5$ | $2.0 \times 10^5$ |
| Molt-4 | $0.5 \times 10^5$ | $0.7 \times 10^5$ | $2.7 \times 10^5$ | | ND | |

*These were used at a dilution of 30% (v/v).

(2) Does not cause lysis of K562 leukemic cell targets which can be determined by such assays as the chromium release assay; and This factor(s) does not affect natural killer (NK) cell cytotoxicity against K-562 targets. (Table VII)

Also this factor inhibits the growth in vitro of cells from certain human tumor cell lines (lung, colon, etc.) (Table VIII).

These SF(s) exhibit a relative molecular weight in the range of 55-70,000, as determined by AcA-44 gel filtration.

Table I-III shows the inhibitory effect of SF on the peripheral blood mononuclear leukocyte proliferative response to mitogens CON A, PWM and PHA. In these examples SF is produced by Jurkat, Molt-4, erythroleukemic cell lines such as K-562 and HPB-ALL cells as well as other cell lines. Cess B cell line generally is positive for SF. In addition, hematopoietic cell hybridomas produce SF.

Supernatants from TT cell hybridomas inhibit the proliferative responses of T-lymphocytes to mitogens such as PHA, CON A, and PWM (Table IX).

T-T cell hybridoma SF also inhibits the proliferative responses of T-cells to allogeneic cells in mixed lymphocyte culture (MLC). (Table X)

Also this factor(s) from T-T cell hybridomas inhibits antibody production of blood cells, and especially in vitro by human peripheral blood mononuclear leukocytes in the PWM-driven system (Table XI). SF may inhibit certain proliferative responses of B-cells.

The action of T-T cell hybridoma SF appears to be cytostatic not cytotoxic since it:

Does not affect the viability of human peripheral blood mononuclear leukocytes in culture after a four day incubation (Table XII).

This factor(s) does not affect natural killer (NK) cell cytotoxicity against K-562 targets. (Table XIII)

These factors are active not only on human but also on mouse cells. (Table XIV)

TT cell SF is not alpha or gamma interferon or lymphotoxin or tumor necrosis factor (TNF).

These SF(s) exhibit a relative molecular weight in the range of 55–70,000, as determined by AcA-44 gel filtration.

TABLE IX

INHIBITION OF PROLIFERATIVE RESPONSES TO PHA BY SUPERNATANTS FROM HUMAN T-T CELL HYBRIDOMAS

| Hybridoma Supernatants (25%) | | CPM | % Suppression |
|---|---|---|---|
| MNC* | | 2,066 ± 341 | — |
| MNC + | | 194,234 ± 9,415 | — |
| PHA | +38F3 | 23,844 ± 2,795 | 88 |
| | +36(38F3) | 29,262 ± 2,333 | 85 |
| | +179(36(38F3)) | 112,580 ± 10,183 | 42 |
| | +180(36(38F3)) | 119,602 ± 14,302 | 38 |
| | +182(36(38F3)) | 29,702 ± 9,005 | 84 |
| | +150(36(38F3)) | 26,141 ± 8,527 | 86 |
| | +151(36(38F3)) | 22,860 ± 5,210 | 88 |
| | +153(36(38F3)) | 14,440 ± 3,306 | 93 |
| | +154(36(38F3)) | 76 ± 20 | 99.9 |
| | +159(36(38F3)) | 10,089 ± 3,145 | 95 |
| | +160(36(38F3)) | 5,710 ± 871 | 97 |
| | +169(36(38F3)) | 10,662 ± 1,902 | 95 |
| | +170(36(38F3)) | 8,179 ± 192 | 96 |
| | +174(36(38F3)) | 58,036 ± 16,330 | 70 |
| | +175(36(38F3)) | 137,108 ± 34,721 | 29 |
| | +176(36(38F3)) | 98,643 ± 15,608 | 49 |
| | +177(36(38F3)) | 143,283 ± 25,986 | 26 |
| | +178(36(38F3)) | 130,097 ± 4,871 | 32 |

*Human peripheral blood mononuclear leukocytes.

| Hybridoma Supernatants* | | CPM | % Suppression |
|---|---|---|---|
| MNC** | | 2,066 ± 341 | — |
| MNC + | | 194,234 ± 9,415 | — |
| PHA | +17F3 | 28,036 ± 1,508 | 86 |
| | +21F3 | 32,403 ± 7,066 | 83 |
| | +31F3 | 12,182 ± 2,751 | 94 |
| | +38F3 | 23,844 ± 2,795 | 88 |
| | +36(38F3) | 29,262 ± 2,333 | 85 |
| | +88F3 | 117,353 ± 20,273 | 39 |
| | +92F3 | 132,662 ± 7,992 | 32 |
| | +181F3 | 92,166 ± 50,145 | 52 |

TABLE IX-continued
INHIBITION OF PROLIFERATIVE RESPONSES TO PHA BY SUPERNATANTS FROM HUMAN T-T CELL HYBRIDOMAS

| | | |
|---|---|---|
| +182F3 | 117,715 ± 43,315 | 38 |

*25% (v/v)
**Human peripheral blood mononuclear leukocytes.

TABLE X
INHIBITION OF PROLIFERATIVE RESPONSES OF HUMAN PERIPHERAL BLOOD MONONUCLEAR LEUKOCYTES TO ALLOGENEIC CELLS IN MIXED LYMPHOCYTE CULTURE BY SUPERNATANTS FROM HUMAN T-T CELL HYBRIDOMAS

| Hybridoma Supernatants (25%) | CPM | | |
|---|---|---|---|
| | A × B | C × D | E × F |
| None | 6086 | 7382 | 5205 |
| 21F3 | 86 | 196 | ND |
| 32F3 | 156 | ND | ND |
| 38F3 | 1252 | 91 | 51 |
| 77(38F3) | 145 | 127 | 150 |
| 181(38F3) | 110 | 146 | ND |
| 36(38F3) | 156 | 59 | 53 |
| 153(36(38F3)) | 82 | 146 | 59 |
| 159(36(38F3)) | 55 | 93 | 57 |
| 160(36(38F3)) | 73 | 141 | 80 |
| 169(36(38F3)) | 61 | 95 | 51 |
| 170(36(38F3)) | 57 | 111 | 81 |

TABLE XI
SUPPRESSION OF IMMUNOGLOBULIN SYNTHESIS AND SECRETION IN THE PWM-INDUCED DIFFERENTIATION SYSTEM BY SUPERNATANTS FROM T-T CELL HYBRIDOMAS

| | Hybridoma Supernatants | IgM (ug/dl) | IgA (ug/dl) | IgG (ug/dl) |
|---|---|---|---|---|
| Mononuclear + PWM leukocytes | None | 189.8 ± 12 | 101.7 ± 5.8 | 66.7 ± 9.7 |
| | +21F3 | 17.4 ± 7.7 | <3.0 | <3.0 |
| | +38F3 | 12.0 ± 4.1 | <3.0 | <3.0 |
| | +181(38F3) | 13.9 ± 4.7 | ND | <3.0 |
| | +77(38F3) | 27.6 ± 6.8 | 39.5 ± 13.1 | 42.0 ± 5.2 |
| | +36(38F3) | 18.7 ± 1.5 | <3.0 | <3.0 |
| | +153(36(38F3)) | 16.5 ± 4.5 | 3.7 ± 1.5 | <3.0 |
| | +159(36(38F3)) | 15.7 ± 3.9 | <3.0 | <3.0 |
| | +160(36(38F3)) | 17.8 ± 2.9 | <3.0 | <3.0 |
| | +168(36(38F3)) | 13.2 ± 3.9 | <3.0 | <3.0 |
| | +169(36(38F3)) | <3.0 | 10.7 ± 5.1 | <3.0 |
| | +170(36(38F3)) | 18.7 ± 1.5 | 11.7 ± 2.5 | <3.0 |

Human peripheral blood mononuclear leukocytes were incubated with PWM and hybridoma supernatants (30%) for seven days at 37C. Supernatants were collected and levels of de novo synthesized IgM, IgA, and IgG were determined by ELISA.

TABLE XII
EFFECT OF SUPERNATANTS FROM HUMAN T-T CELL HYBRIDOMAS ON THE VIABILITY OF HUMAN PERIPHERAL BLOOD MONONUCLEAR LEUKOCYTES

| Hybridoma Supernatants | % Viability Incubation Time | | | |
|---|---|---|---|---|
| | 20 hrs | 44 hrs | 68 hrs | 88 hrs |
| None | 98 | 100 | 96 | 93 |
| 21F3 | 98 | 97 | 97 | 95 |
| 38F3 | 99 | 97 | 95 | ND |
| 32(38F3) | 97 | 98 | 98 | 95 |
| 77(38F3) | 100 | 96 | 92 | 89 |
| 181(38F3) | 98 | 98 | 97 | 91 |
| 36(38F3) | 98 | 98 | 93 | 91 |
| 153(36(38F3)) | 98 | 96 | 98 | 93 |
| 159(36(38F3)) | 98 | 98 | 95 | ND |
| 160(36(38F3)) | 99 | 100 | 95 | 94 |
| 168(36(38F3)) | 99 | 96 | 93 | 93 |
| 169(36(38F3)) | 100 | 97 | 99 | 95 |
| 170(36(38F3)) | 100 | 99 | 95 | 95 |

Human peripheral blood mononuclear leukocytes were cultured with 30% supernatants from T-T cell hybridomas, washed twice and viability was determined by trypan blue dye exclusion.

TABLE XIII
EFFECT OF SUPERNATANTS FROM T-T CELL HYBRIDOMAS ON NATURAL KILLER CYTOTOXICITY

| Hybridoma Supernatants | % CYTOTOXICITY | | | |
|---|---|---|---|---|
| | Donor 1 | | Donor 2 | |
| | 50:1 | 25:1 | 50:1 | 25:1 |
| Medium | 66 | 59 | 58 | 50 |
| 17F$_3$* | 63 | 56 | 57 | 42 |
| 36(38F$_3$)* | 57 | 48 | 45 | 43 |
| 77(38F$_3$)* | 64 | 50 | 47 | 47 |
| 159(36(38F$_3$)) | 59 | 55 | 54 | 38 |
| 168(36(38F$_3$)) | 59 | 50 | 45 | 38 |
| 101(38F$_3$) | 60 | 55 | 48 | 44 |
| 102(38F$_3$) | 59 | 57 | 49 | 35 |

*Supernatants with suppressor activity.

TABLE XIV
INHIBITION OF PROLIFERATIVE RESPONSES OF BALB/C MOUSE THYMOCYTES TO CON A, BY SUPERNATANTS FROM HUMAN T-T CELL HYBRIDOMAS

| Supernatant concentration (% v/v) | Counts per Minute T-T Cell Hybrid Supernatants | | | | | |
|---|---|---|---|---|---|---|
| | 159(36(38F3)) Con A | | 36(38F3) Con A | | 169(86(38F3)) Con A | |
| | 3 μg/ml | 6 μg/ml | 3 μg/ml | 6 μg/ml | 3 μg/ml | 6 μg/ml |
| Thymocytes | 89,930 | 254,180 | 89,930 | 254,180 | 89,930 | 254,180 |
| Thymocytes +2.5% | 8,295 | 15,435 | 36,510 | 93,573 | 166,300 | 247,600 |

TABLE XIV-continued
INHIBITION OF PROLIFERATIVE RESPONSES OF BALB/C MOUSE THYMOCYTES TO CON A, BY SUPERNATANTS FROM HUMAN T-T CELL HYBRIDOMAS

| | Counts per Minute T-T Cell Hybrid Supernatants | | | | | |
|---|---|---|---|---|---|---|
| Supernatant concentration | 159(36(38F3)) Con A | | 36(38F3) Con A | | 169(86(38F3)) Con A | |
| (% v/v) | 3 μg/ml | 6 μg/ml | 3 μg/ml | 6 μg/ml | 3 μg/ml | 6 μg/ml |
| Thymocytes +5% | 3,050 | 3,553 | 40,708 | 82,791 | 180,519 | 302,994 |
| Thymocytes +10% | 3,271 | 2,242 | 13,366 | 14,998 | 192,006 | 286,007 |
| Thymocytes +20% | 4,132 | 2,700 | 7,531 | 7,736 | 202,671 | 298,623 |

The HLA type of the T-T cell hybridomas is shown in Table XV.

Some T-T cell hybridomas produce B-cell growth factor. These results are shown in table XVI. These hybridomas are different from the cells which produce SF.

These examples are for illustrative purposes only and are not meant to limit the invention.

TABLE XV
HLA TYPING OF HUMAN T-T CELL HYBRIDOMAS

| | Fusion Cell HLA: |
|---|---|
| Donor: | A9, 19; B5, 12 |
| Jurkat: | A2; B7, 15 |
| | T-T Cell Hybridoma HLA: |
| 21F3: | A9, 19; B7, 12 |
| 75(38F3): | A19; B5, 7 |
| 13(185(38F3)): | A2, 9; B7, 12 |
| 22(185(38F3)): | A9, 19; B5, 7, 15 |
| 153(36(38F3)): | A9, 19; B12 |
| 169(36(38F3)): | A2,19; B7, 12 |
| 170(36(38F3)): | A9, 19; B5, 7, 12 |

TABLE XVI
HUMAN T-T CELL HYBRIDOMAS CONSTITUTIVELY PRODUCING B-CELL GROWTH FACTOR (BCGF)

| | | Hybridoma Supernatants | CPM Donor 1 | CPM Donor 2 |
|---|---|---|---|---|
| E-rosette negative cells | | None | 1,843 ± 329 | 223 ± 99 |
| >> | + SAC | None | 41,152 ± 3,815 | 1,228 ± 158 |
| >> | + SAC | 15F3 | 44,143 ± 3,395 | 3,743 ± 774 |
| >> | + SAC | 16F3 | 37,538 ± 4,364 | 5,478 ± 379 |
| >> | + SAC | 56F3 | 41,547 ± 4,247 | 2,899 ± 613 |
| >> | + SAC | 41F3 | 39,571 ± 2,288 | 3,081 ± 489 |
| >> | + SAC | 24F3 | 225,288 ± 23,904 | 47,744 ± 2,198 |
| >> | + SAC | 32F3 | ND | 274,999 ± 55,710 |
| >> | + SAC | 36F3 | ND | 157,874 ± 24,865 |
| >> | + SAC | 206F3 | ND | 243,662 ± 23,983 |
| >> | + SAC | 64F3 | ND | 253,039 ± 35,711 |

Proportion of hybridomas constitutively producting BCGF: 7–10%
Stability: one to two months

What is claimed:

1. A method for production of human T-T cell hybrids which produce Suppressor Factor wherein cells of lymphoid origin are fused with comprises:
   (a) mixing cells from a first parent cell line comprising a non-mutagenized Jurkat lymoblastoid T cell line, wherein the Jurkat lymphoblastoid cells are not sensitive and cannot be killed by hypoxanthine-aminopterin-thymidine medium, with a second parent cell comprising mitogen or alloantigen activated peripheral blood leukocyte T cells or purified T-cels,
   (b) allowing the first and second parent cells to fuse in the presence of polyethylene glycol for about 10–20 minutes with gentle agitation to generate hybrids in the cell mixture,
   (c) incubating the cell mixture containing the hybrids and the first and second parent cells, after removal of the polyethylene glycol, for periods fo between one to sixty days at 37° in 5% $CO_2$,
   (d) selecting for the hybrids by separating the hybrids from the first parent Jurkat lymphoblastoid cells by coloning in agar medium wherein the hybrids form colonies,
   (e) recovering the hybrids that form colonies in agar medium and expanding them in culture, and
   (f) determining the presence of Supressor Factor in the culture and recovering the T-T cell hybrids which produce suppressor factor.

2. Method of claim 1 wherein the incubation of cells in step (c) is for a period of time selected from the group consisting of 10, 15 and 20 days.

3. Suppressor Factor produced by hybrid T-T cells which hybrids are produced according to the method of claim 1, wherein said suppressor Factor:
   (1) inhibits proliferative response of T-lymphocytes to mitogens selected from the group consisting of phytohemagglutinin, concanavalin A and Pokeweed mitogen,
   (2) inhibits proliferative response of T-cells to allogenic cells in mixed lymphocyte culture,
   (3) substantially inhibits antibody production of human blood cells,
   (4) inhibits greater than 80% IgG, IgA and IgM anitbody production in vitro by human peripheral blood mononuclear leukocytes in a pokeweed mitogen-driven systems,
   (5) inhibits proliferative respnses of B-cells,
   (6) does not affect viability of human peripheral blood mononuclear leukocytes,
   (7) does not affect killer cell cytoxicity against K-562 targets,
   (8) is free of lymphotoxin, tumor necrosis factor or alpha or gamma-interferon,
   (9) has a relative molecular weight of 55,000–70,000 as determined by gel filtration, and
   (10) is produced from T-T cell hybridomas having cell surface phenotype T3+, T4+, T8−.

* * * * *